United States Patent [19]
Mikhail

[11] Patent Number: 5,549,701
[45] Date of Patent: Aug. 27, 1996

[54] ACETABULAR CUP

[76] Inventor: W. E. Michael Mikhail, 4203 Shamley Green, Toledo, Ohio 43623

[21] Appl. No.: 412,615

[22] Filed: Mar. 29, 1995

Related U.S. Application Data

[63] Continuation of Ser. No. 129,956, Sep. 30, 1993, abandoned.

[51] Int. Cl.⁶ .................................. A61F 2/34; A61F 2/30
[52] U.S. Cl. ................................................ 623/22; 623/18
[58] Field of Search ......................... 623/16, 18, 19, 623/20, 21, 22, 23

[56] References Cited

U.S. PATENT DOCUMENTS

| | | | |
|---|---|---|---|
| 3,829,904 | 8/1974 | Ling et al. | 3/1.91 |
| 3,986,212 | 10/1976 | Sauer | 3/1.91 |
| 4,040,131 | 8/1977 | Gristina | 3/1.91 |
| 4,281,420 | 8/1981 | Raab | 3/1.91 |
| 4,296,714 | 10/1981 | Büchner | 123/53 |
| 4,380,090 | 4/1983 | Ramos | 3/1.91 |
| 4,491,987 | 1/1985 | Park | 3/1.91 |
| 4,596,580 | 6/1986 | Weill | 623/22 |
| 4,695,282 | 9/1987 | Forte et al. | 623/22 |
| 4,704,127 | 11/1987 | Averill et al. | 623/22 |
| 4,883,490 | 11/1989 | Oh | 623/22 |
| 4,904,267 | 2/1990 | Bruce et al. | 623/23 |
| 4,997,447 | 3/1991 | Shelley | 623/22 |
| 5,002,577 | 3/1991 | Bolesky et al. | 623/22 |
| 5,009,665 | 4/1991 | Serbousek et al. | 623/22 |
| 5,019,105 | 5/1991 | Wiley | 623/22 |
| 5,021,062 | 6/1991 | Adrey et al. | 623/22 |
| 5,021,063 | 6/1991 | Täger | 623/23 |
| 5,049,158 | 9/1991 | Engelhardt et al. | 623/22 |
| 5,080,677 | 1/1992 | Shelley | 623/22 |
| 5,092,897 | 3/1992 | Forte | 623/22 |
| 5,171,243 | 12/1992 | Kashuba et al. | 606/86 |
| 5,171,285 | 12/1992 | Broderick | 623/22 |
| 5,171,286 | 12/1992 | Lawes et al. | 623/22 |
| 5,176,711 | 1/1993 | Grimes | 623/22 |
| 5,192,329 | 3/1993 | Christie et al. | 623/22 |
| 5,197,989 | 3/1993 | Hinckfuss et al. | 623/23 |
| 5,226,917 | 7/1993 | Schryver | 623/22 |

FOREIGN PATENT DOCUMENTS

| | | | |
|---|---|---|---|
| 0065482 | 11/1982 | European Pat. Off. | 623/22 |
| 0091315 | 10/1983 | European Pat. Off. | 623/22 |
| 0253941 | 1/1988 | European Pat. Off. | 623/22 |
| 0313773 | 8/1989 | European Pat. Off. | 623/22 |
| 2649005 | 1/1991 | France | 623/22 |
| 2154141 | 9/1985 | United Kingdom | 623/22 |

OTHER PUBLICATIONS

Catalog of Osteonics Corp., 59 Route 17, Allendale, NJ entitled "Cemented Acetabular Cup—Surgical Protocol", copyright 1992.
Catalog of Howmedica International entitled "Exeter Total Hip System" (date of publication unknown).
The following articles from vol. 19, No. 3, Jul. 1988 entitled "The Orthopedic Clinics of North America—Long—Term Results of Cemented Joint Replacement" published by W. B. Saunders Company, Philadelphia, PA.
N. Eftekhar et al., "Incidence and Mechanism of Failure of Cemented Acetabular Component in Total Hip Arthoplasty", pp. 557–566.
C. Ranawat et al., "Effect of Modern Cement Technique on Acetabular Fixation Total Hip Arthroplasty", pp. 599–603.
B. M. Wroblewski, "Wear and Loosening of the Socket in the Charnley Low–Friction Anthroplasty", pp. 627–636.
M. D. Fuchs et al., "Results of Acetabular Revisions with Newer Cement Techniques", pp. 649–655.

*Primary Examiner*—David Isabella
*Attorney, Agent, or Firm*—Emch, Schaffer, Schaub & Porcello

[57] ABSTRACT

An acetabular cup member is suitable for use in direct cemented implantation with the bone or as an insert for a metal shell component of an acetabular cup assembly.

13 Claims, 9 Drawing Sheets

ACETABULAR CUP

This is a continuation of application Ser. No. 08/129,956 filed on Sep. 30, 1993, now abandoned.

BACKGROUND ART

The present invention relates to an acetabular cup for receiving the ball of a femoral hip joint prosthesis.

Acetabular cups and acetabular cup assemblies of various types have long been used in hip joint replacement surgery. In such surgery, a femoral hip joint prosthesis formed of a suitable metal such as a cobalt chrome molybdenum alloy or other FDA approved material is implanted in the femur. The femoral hip joint prosthesis has an associated spherical-shaped ball. It is necessary to implant an acetabular cup or acetabular cup assembly in the acetabulum in a cavity which has been prepared by the surgeon for the purpose of receiving the spherical-shaped ball.

The artificial socket (i.e., acetabular cup or acetabular cup assembly) in which the ball of the femoral hip joint prosthesis is to be positioned is formed of a material other than metal and is frequently formed of a suitable biocompatible plastic such as a high molecular weight polyethylene (HMWPE) as this provides a natural lubricity which permits the ball to freely rotate in the cup socket.

In some instances, the acetabular cup is a single unitary device which is implanted in a prepared cavity of the acetabulum using a suitable bone cement such as polymethylmethacrylate (PMMA). In other instances, depending upon the condition of the patient and/or the preference of the surgeon, an acetabular cup assembly consisting of multiple units including a metal shell and a plastic cup-shaped insert may be used. In the latter instance, the metal shall may be affixed in the prepared cavity of the acetabulum by a variety of means including screws joining the metal shell directly to the acetabulum or a friction fit in the cavity with a shell having an exterior surface of a type which is roughened, coated or formed with interstices which will promote bone ingrowth therein. Examples of one-piece acetabular cups are shown in U.S. Pat. Nos. 3,829,904; 3,986,212 and the FIG. 1 embodiment of U.S. Pat. No. 5,009,665. Examples of multiple-piece acetabular cup assemblies are shown in the FIGS. 2–4 embodiments of U.S. Pat. No. 5,009,665 and in U.S. Pat. Nos. 4,704,127; 4,695,282; 5,002,577 and 5,019,105. The foregoing prior art patents are hereby incorporated by reference in this application.

Heretofore, plastic cup members intended for use as a single unitary unit were manufactured to one of various designs depending upon the manufacturer and plastic cup members intended for use with a separate shell member to form an acetabular cup assembly were designed and manufactured to different configurations even in those instances where a single manufacturer produced both the unitary type and the multiple component assembly type of acetabular cup prosthesis. This, of course, required that the manufacturer have one mold for forming a plastic member intended for the unitary acetabular cup prosthesis and a different mold for forming the plastic cup member of the same size intended for use with a metal shell for an acetabular cup assembly. As is well known, the plastic acetabular cups come in a wide variety of sizes and a separate mold is required for each size cup. Heretofore, the fact that different designs of plastic acetabular cups were used for unitary acetabular cup prostheses than for acetabular cup assemblies required that the hospital carry separate inventories of plastic cups, one set for the unitary version and a second set for the multiple component version, with several sizes required for each such set.

DISCLOSURE OF THE INVENTION

The present invention is directed to an acetabular cup member which is suitable for use either in direct cemented implantation with the bone or as an insert for a metal shell component of an acetabular cup assembly. Since the same plastic cup member of the present invention may be used either as a single element acetabular cup prosthesis cemented in the prepared cavity of the acetabulum or as a component with a metal shell affixed in the prepared cavity of the acetabulum, the hospital is required to carry only one type of plastic acetabular cup member for each size rather than two.

Accordingly, it is an object of the present invention to provide an acetabular cup member which is suitable for use in direct cemented implantation in a prepared cavity of an acetabulum or as an insert for a metal shell affixed in a prepared cavity of an acetabulum.

It is a further object of the present invention to provide a acetabular cup member having an exterior surface having irregularities which permits its use as a unitary prosthesis in a prepared cavity of an acetabulum and retained therein by bone cement in direct contact with such unitary cup member or as the liner of a metal socket cooperating to form an acetabular cup assembly intended for retention by ingrowth of the bone therein or by screws.

Other objects and advantages of the present invention will become readily apparent from the following detailed description of the drawings.

BRIEF DESCRIPTION OF THE DRAWINGS

FIG. 11 is an elevational view of a metal shell of the type shown in the FIG. 8 embodiment.

FIG. 11 is a fragmentary view looking in the direction of line 11A—11A of FIG. 11.

BEST MODE OF CARRYING OUT INVENTION

Figure 1:
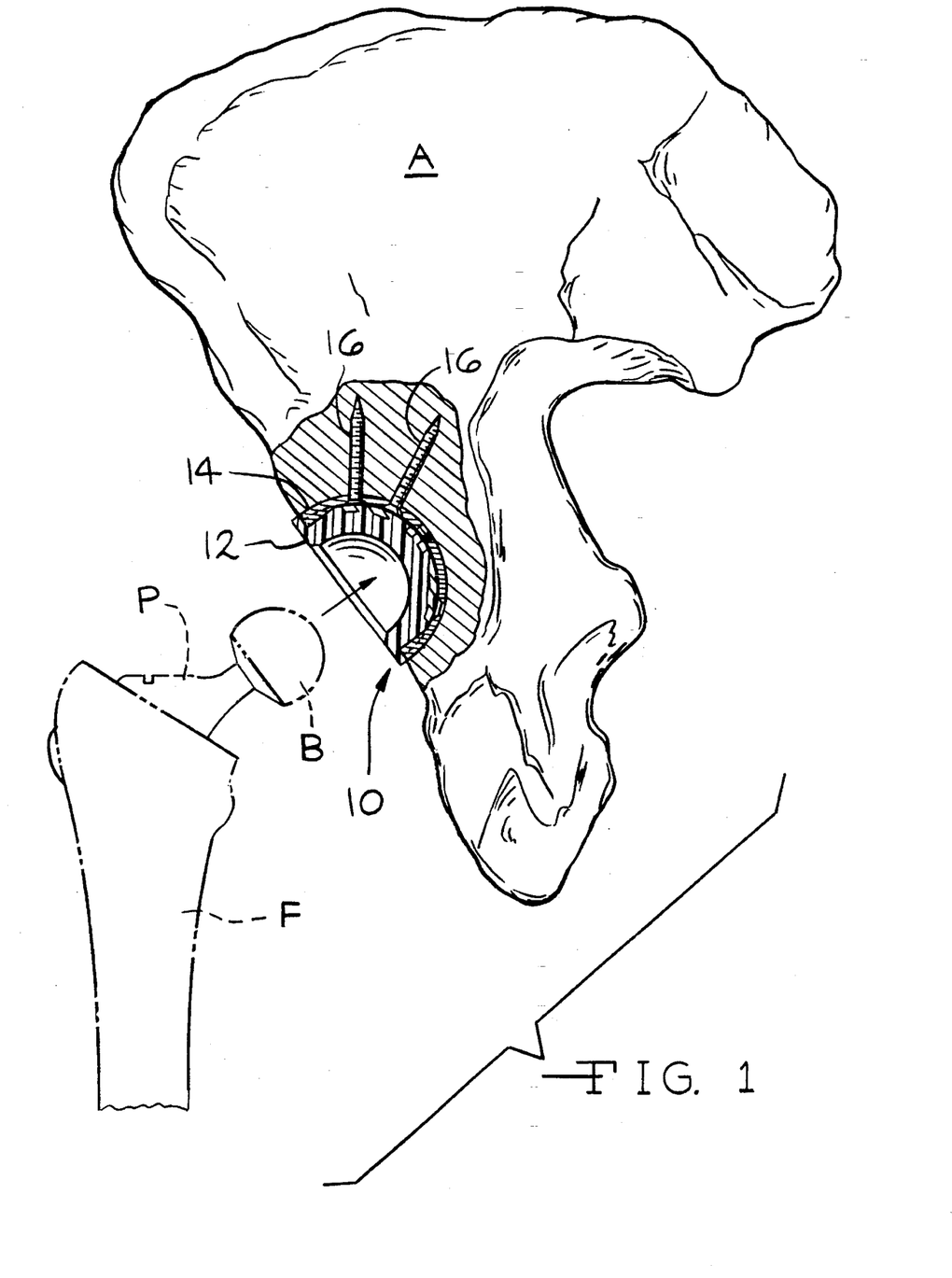
FIG. 1 is a schematic view showing one version of the present invention with a metal shell affixed by screws in a prepared cavity of the acetabulum and with the acetabular cup member positioned therein ready to receive a spherical ball of a femoral hip joint prosthesis.

Referring now to FIG. 1, there is shown an acetabulum A in which has been implanted an acetabular cup assembly generally designated by the numeral 10. The acetabular cup assembly 10 shown in FIG. 1 includes an acetabular cup member 12 which is preferably formed of a polymer such as HMWPE but which may also be formed of a ceramic or other suitable non-metallic material. The acetabular cup member 12 is assembled to a metal shell 14 which is affixed in a prepared cavity of the acetabulum by two or more screws 16.

The acetabular cup member 12 is shown as being prepared to receive a spherical ball B of a femoral hip joint prosthesis P which has been implanted in a femur F.

Figure 2:
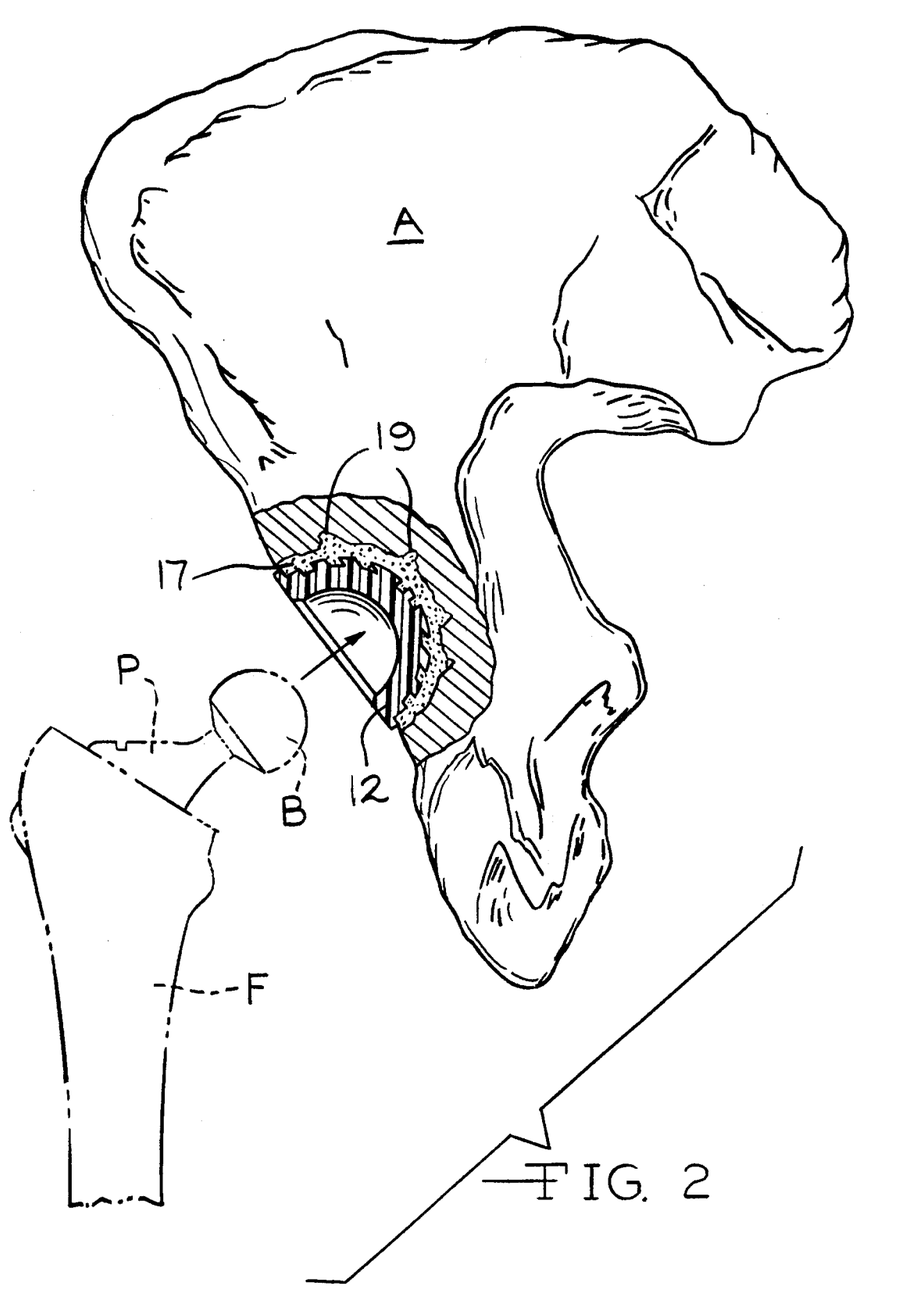
FIG. 2 is a view similar to FIG. 1 showing a unitary acetabular cup member of the present invention affixed directly in a prepared cavity of the acetabulum with bone cement.
Figure 3:
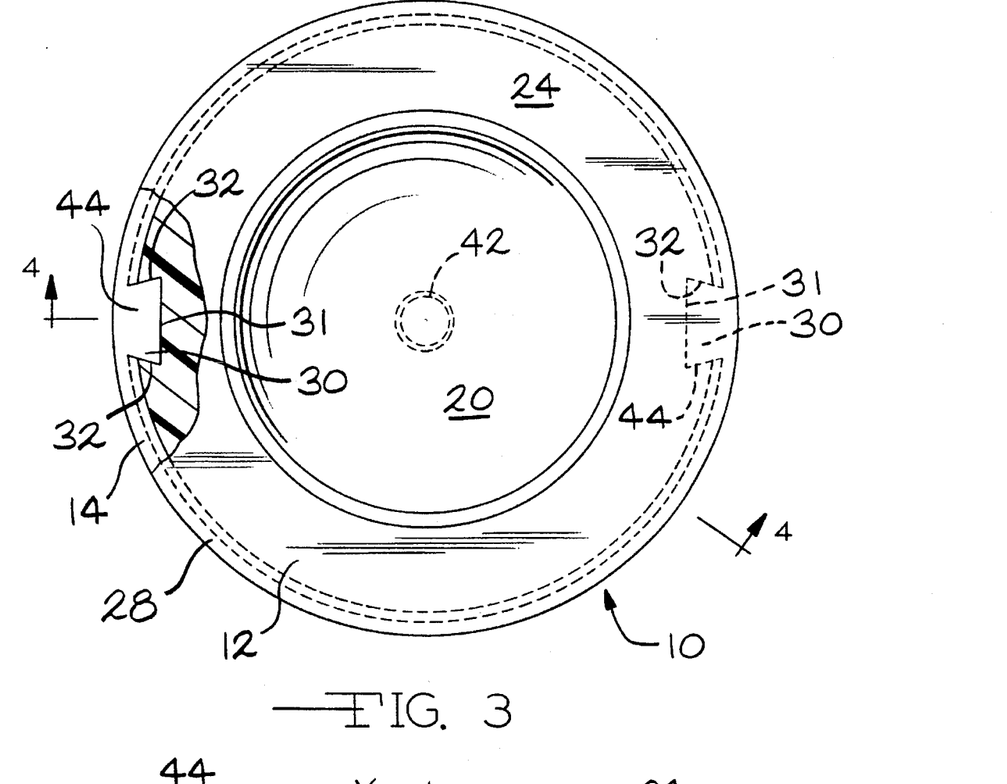
FIG. 3 is a plan view, partly in section, of the acetabular cup assembly of FIG. 1.
Figure 4:
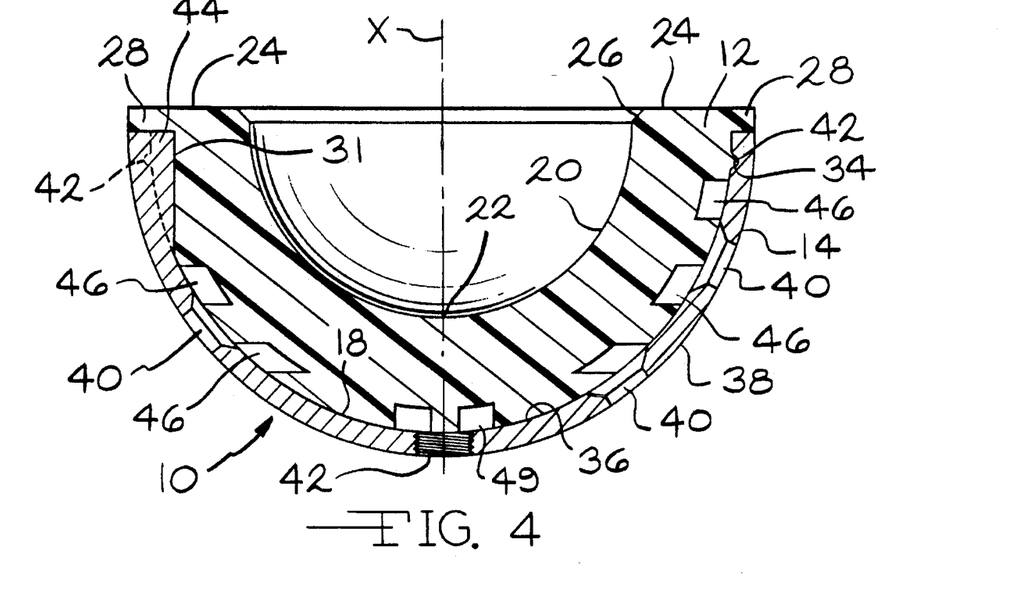
FIG. 4 is a view taken through line 4—4 of FIG. 3.

FIG. 2 shows the identical plastic acetabular cup member 12 functioning as a unitary prosthesis and implanted directly in the prepared cavity of the acetabulum A with bone cement 17. The cavity preferably has been formed with irregularities 19 to provide for good retention of the bone cement 17.

Referring now to FIGS. 3–7, the acetabular cup member 12 of the present invention includes an exterior face 18 and an interior face 20. The acetabular cup member 12 is symmetrical about an axis X. The interior face 20 is smooth and has a major portion having a spherical configuration with an apex 22 lying on the axis X. The acetabular cup member 12 includes a planar edge 24 which is joined to the spherical-shaped interior face 20 by a chamfer 26. Preferably, the spherical portion of the interior face 20 is a full hemisphere. Preferably, the planar edge 24 extends beyond the exterior face 18 to form a flange 28 which, extends annularly around the exterior face 18. Under this embodiment, there are provided both means for engaging the acetabular cup member 12 to the metal shell 14 when the cup member 12 is used as an element of an acetabular cup assembly 10 and means for engagement of the cup member 12 by bone cement when it is used as a unitary prosthesis.

The means for affixing the cup member 12 to a metal shell 14 comprise a pair of dovetail slots 30 each having a rear wall 31 extending substantially parallel to the axis X and a pair of side walls 32 angling with respect to one another such that they are spaced further apart at their respective points of juncture with the rear wall 31 and taper inwardly towards each other in a direction away from such rear wall. The exterior face 18 is also provided with an outwardly extending bead 34 spaced below the edge 24 and its flange 28 and, except for the area of the dovetail slots 30, extending completely around the exterior face 18 in that area.

The metal shell 14 is cup-shaped and has an interior face 36 with a configuration designed to snugly receive the outermost portion of the exterior face 18 of the acetabular cup member 12. The shell 14 also has an exterior face 38 substantially parallel to the interior face 36 and has a plurality of apertures 40 for receiving the screws 16. The shell 14 also has a threaded aperture 42 at its apex along the axis X which may be used for insertion in the prepared cavity or for extraction in the event subsequent revision surgery is required. The metal shell 14 is provided with an annular groove 42 for receiving the bead 34 of the acetabular cup member 12 and a pair of dovetail-shaped ribs 44 intended to be positioned and sized to be received in the dovetail slots 30 of the acetabular cup member 12.

Figure 5:
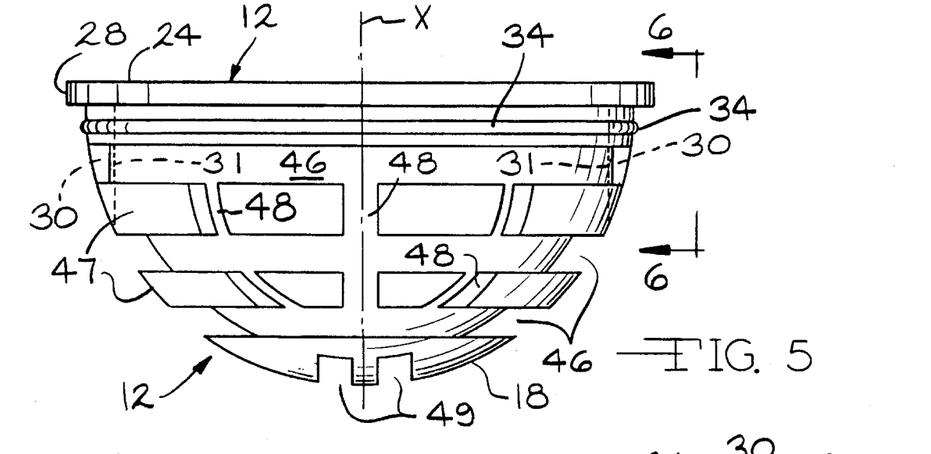
FIG. 5 is an elevational view of the acetabular cup member which is usable either with the shell as shown in FIG. 1 or as a unitary prosthesis as shown in FIG. 2.
Figure 6:
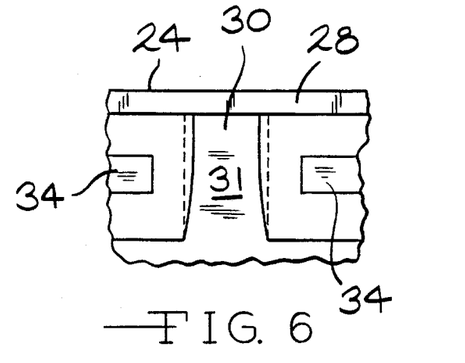
FIG. 6 is an enlarged fragmentary view of the plastic acetabular cup member looking in the direction of line 6—6 of FIG. 5 and showing a dovetail groove which can be engaged by a corresponding dovetail rib of a metal shell when used as a component of a multiple unit acetabular cup assembly.
Figure 7:
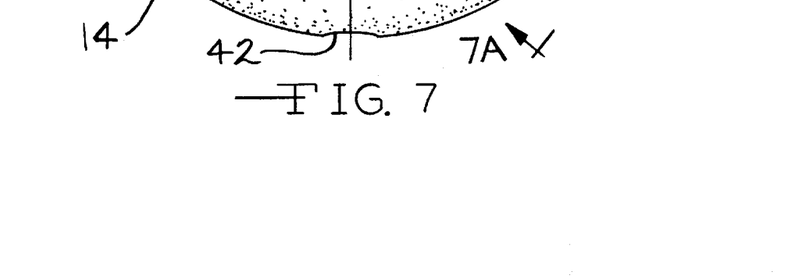
FIG. 7 is an elevational view of a metal shell of the type shown in FIG. 4.
Figure 7A:
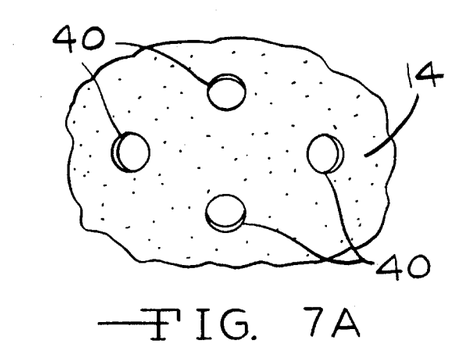
FIG. 7A is a fragmentary view looking in the direction of line 7A—7A of FIG. 7.

Referring particularly to FIG. 5, there is shown one type of means for engaging the acetabular cup member 12 in bone cement when it is used as a unitary prosthesis. There are provided three rows of annular grooves 46 which are substantially perpendicular to the axis X and are separated by ribs 47. Additionally, the rows of grooves 46 may be joined together by grooves 48 extending toward the apex 22 and defining planes which extend through the axis X. Additional grooves 49 may be formed therein adjacent the apex of the exterior face 18.

As can be seen in FIG. 2, when the acetabular member 12 is used as a unitary prosthesis without the metal shell, the bone cement 17 fills in the grooves 46, 48 and 49 and serves to retain the acetabular cup member 12 in the cavity formed in the acetabulum A.

Figure 8:
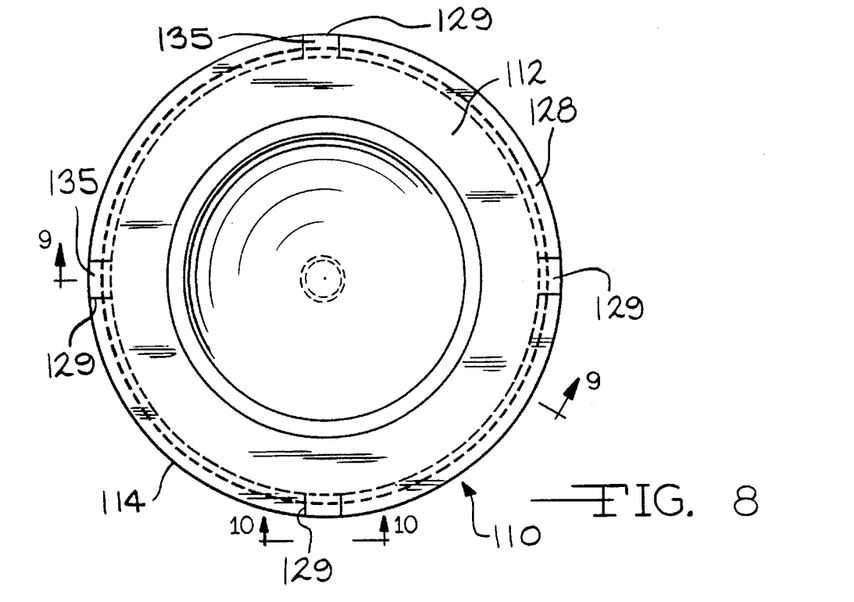
FIG. 8 is a plan view of another embodiment of an acetabular cup member showing it assembled with a metal shell.
Figure 9:
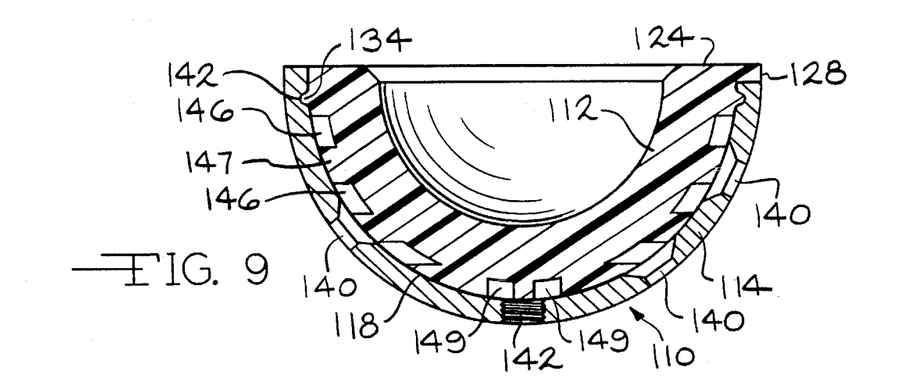
FIG. 9 is a sectional view taken through line 9—9 of FIG. 8.
Figure 10:
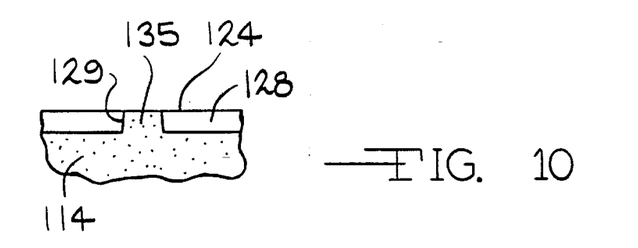
FIG. 10 is an fragmentary view looking in the direction of line 10—10 of FIG. 8.
Figures 11, 11A:
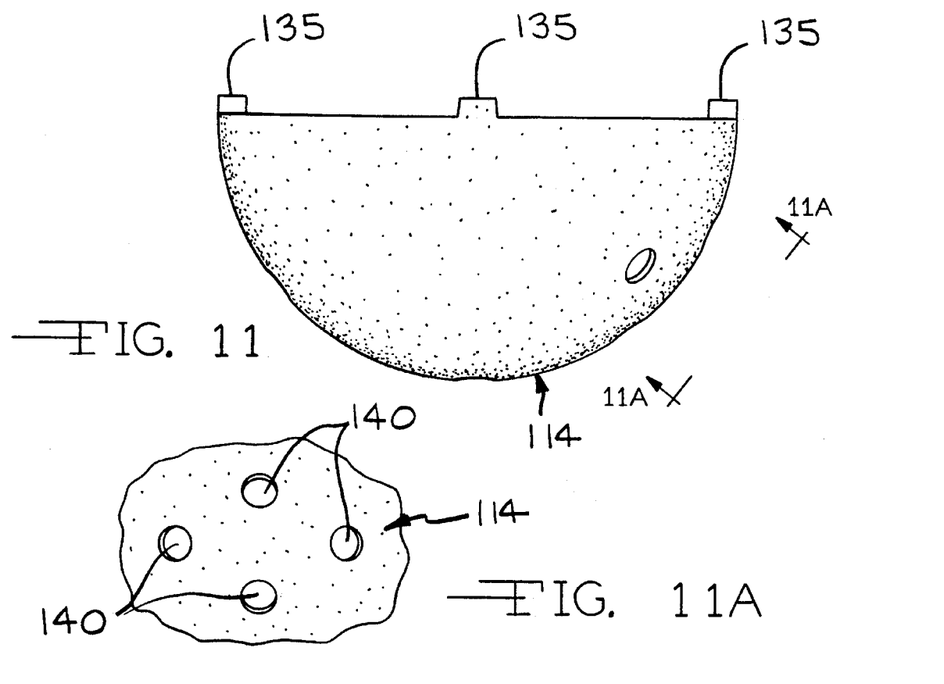

Referring now to FIGS. 8–12, there is shown a modified embodiment of the acetabular cup member of the present invention. FIGS. 8–10 show the acetabular cup member 112 assembled in a shell 114 to form an acetabular cup assembly 110. The acetabular cup member 112 may be used as a unitary element and implanted directly in a prepared cavity of an acetabulum using bone cement. As such, the exterior face 118 is provided with grooves 146 separated by ribs 147 and joined together by grooves 148 as in the embodiment of FIGS. 1–7. Additional grooves 149 are also provided on opposite sides of the apex.

Figure 12:
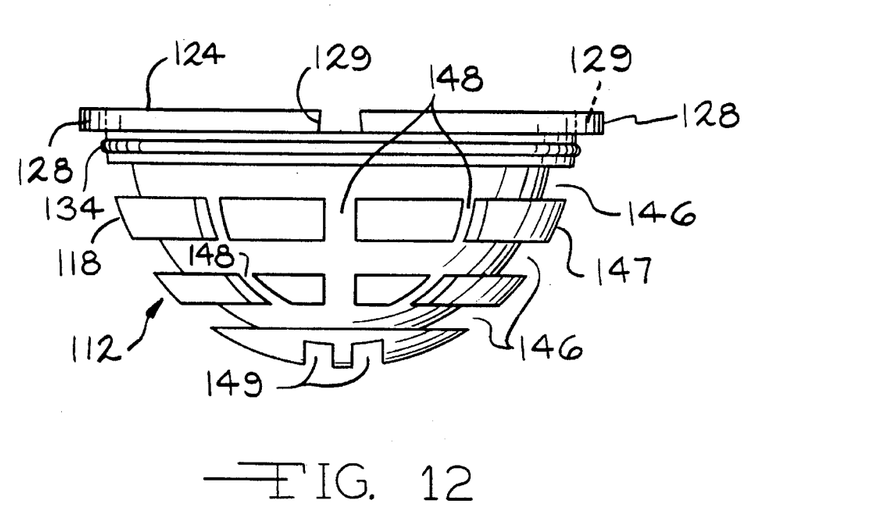
FIG. 12 is an elevational view of a an acetabular cup member of the type used in the FIG. 8 embodiment.

Extending outwardly from the exterior face 118 at the edge 124 is a flange 128. The flange 128 is provided with a plurality of slots 129. As shown in FIG. 8, there are four slots 129. There could be a greater number of lesser number of such slots; however, it is greatly preferred that there be at least two such slots 129. The acetabular cup member 112 also has a bead 134 extending around the exterior face 118 in spaced parallel relationship with the flange 128.

In the event it is desired to use the acetabular cup member 112 as a component in an acetabular cup assembly, it will be affixed to a metal shell 114 which is identical to the metal shell 14 of the previous embodiment with the exception that the metal shell 114 has a plurality of upwardly extending lugs 135 which are positioned in spaced apart relationship such that they will engage the slots 129 of the flange 128 when the acetabular cup member 112 is positioned therein. As in the previous embodiment, the bead 134 engages an inwardly facing groove 142 of the metal shell 114. The metal shell 14 also has a plurality of screw receiving apertures 140 and a threaded aperture 142.

Referring now to FIGS. 13–17, there is shown yet another embodiment of acetabular cup assembly 210 and acetabular cup member 212 which may be used as a component for such assembly or as a unitary acetabular cup with no metal shell for direct implantation in cement in the prepared cavity of the acetabulum. Under the embodiment of FIGS. 13–17, the acetabular cup member 212 is provided with an exterior face 218 having grooves 246, 248 and 249 and ribs 247 as in the previous embodiments. It also has an annular flange 228 extending outwardly therefrom at the edge 224. Immediately below the annular flange 228 are a series of sawtooth members 250. Adjacent the sawtooth members 250 on the opposite side thereof from the flange 228 is a screw thread 256. As can be seen from FIG. 13, the sawtooth members 250 are angled in a direction permitting the acetabular cup member 212 to be screwed into a member having a similar sawtooth members but preventing the unscrewing thereof. Preferably, the sawtooth members 250 have rounded ends.

Figure 13:
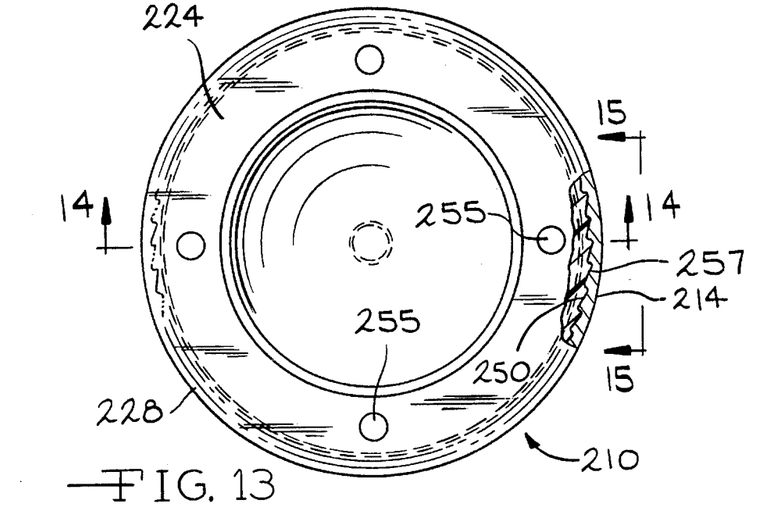
FIG. 13 is a plan view of yet another embodiment of acetabular cup member showing it assembled with a metal shell.
Figure 17:
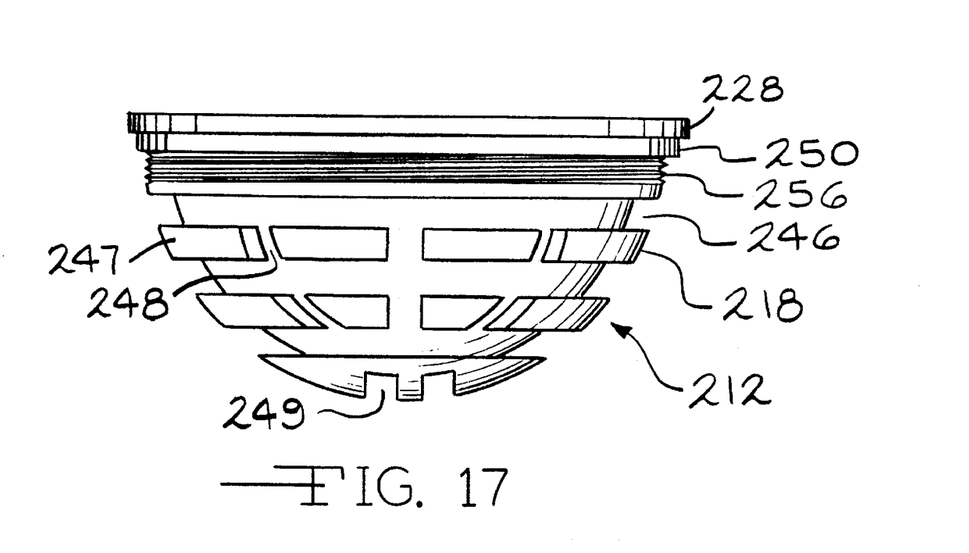
FIG. 17 is an elevational view of the acetabular cup member of the FIG. 13 embodiment.

A plurality of recesses 255 are formed in the edge 224. The recesses 255 are positioned such that they may be engaged by a spanner wrench in order to screw the acetabular cup member 212 in position when used with a metal shell.

When the acetabular cup member 212 is used as a component of an acetabular cup assembly 210, a metal shell 214 is provided. The metal shell 214 is similar to the metal shell 14 of the embodiment of FIGS. 1–8; however, it is provided with a series of sawtooth members 257 extending around the shell interior 220 in a position to be engaged by the sawtooth members 250 of the acetabular cup member 212. Beneath the sawtooth members 257 of the metal shell 214 is a thread 258 positioned to be engaged by the thread 256 of the acetabular cup member 212. As can be seen from FIG. 13, the angle of the sawtooth members 257 of the metal shell 214 are similar to the angle of the sawtooth members 250 of the acetabular cup member 212 such that the acetabular cup member 212 can be readily screwed into the metal shell 214 due to the resiliency of the plastic material from which the acetabular cup member is made but cannot be removed therefrom.

Figure 14:
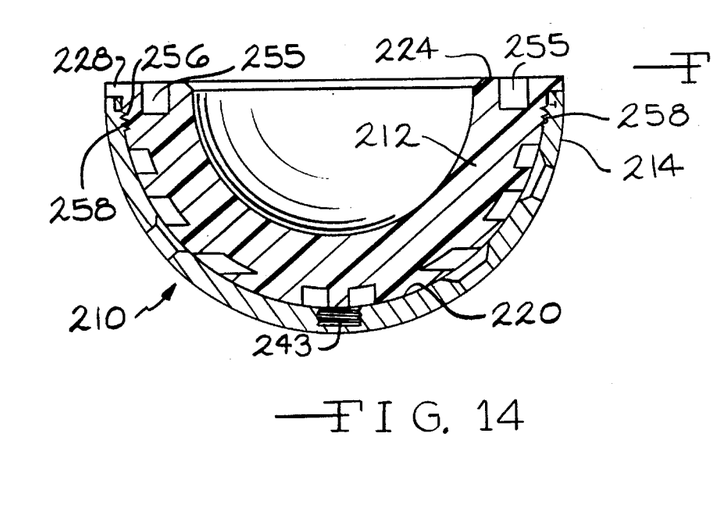
FIG. 14 is a sectional view taken through line 14—14 of FIG. 13.
Figure 15:
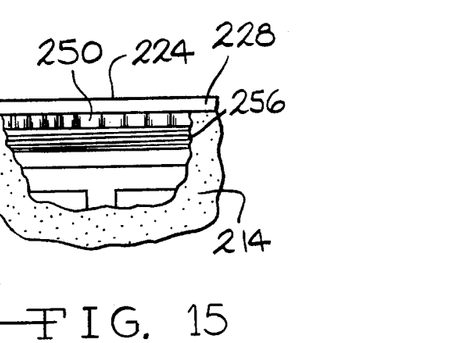
FIG. 15 is an enlarged fragmentary view looking in the direction of the arrows of line 15—15 of FIG. 13.

The sawtooth members 250 and 257 and the threads 256 and 258 are made in such a way as to avoid formation of particulate debris or shredded particles in the course of assembling the acetabular cup member 212 to the shell 214. For example, the sawtooth members 250 and 257 are formed with rounded ends. Additionally, sharp edges are avoided on the threads 256 and 258. It is important to avoid the formation of particulate debris as its formation leads to micromigration thereof which can cause corrosion.

Figure 16:
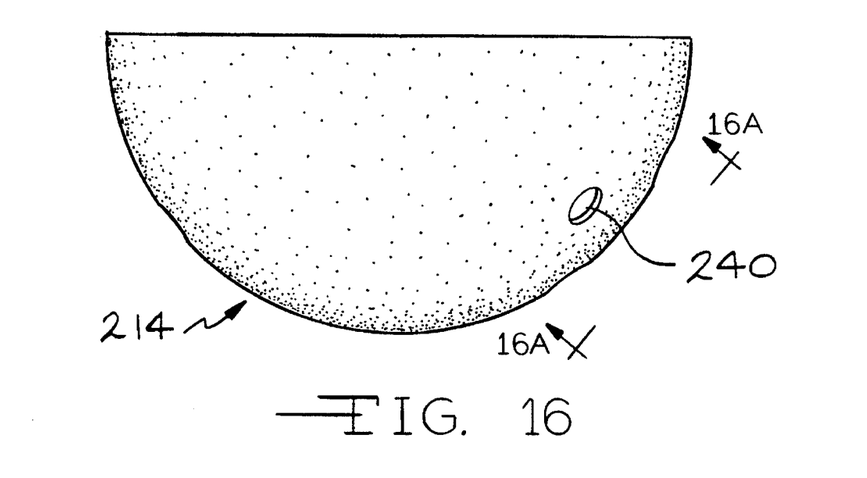
FIG. 16 is an elevational view of a metal shell of the type shown in the FIG. 13 embodiment.
Figure 16A:
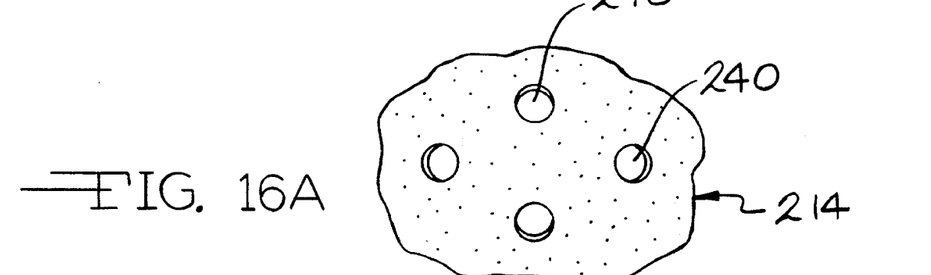
FIG. 16A is a fragmentary view looking in the direction of line 16A—16A of FIG. 16.

The metal shell 214 is provided with a threaded, dead-end recess 243 at its apex. The threaded recess 243 extends from the interior face 236 through 60% to 80% of the thickness of the shell 214 and is available for use by the surgeon with a threaded tool for insertion of the metal shell 214 during implantation or removal of the metal shell 214 in the event subsequent removal thereof is required.

Figure 18:
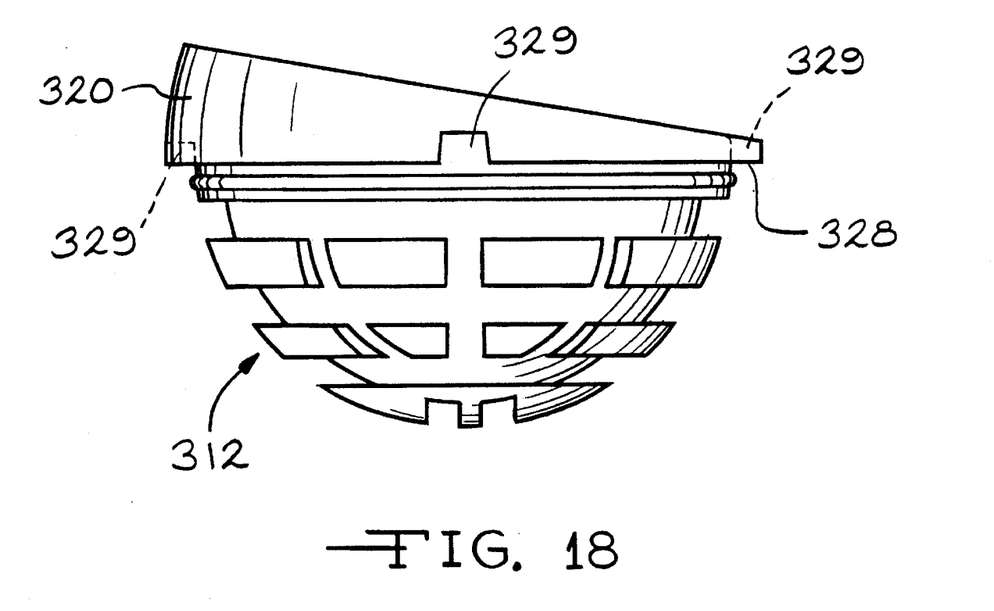
FIG. 18 is an elevational view of another embodiment of the acetabular cup member.

Referring now to FIG. 18, there is provided yet another embodiment of acetabular cup member 312 which is identical to the acetabular cup member 112 of FIG. 12 with the exception that it is provided with an extended rim 320 which extends upwardly from the flange 328 at an angle of 5° to 10° from the lower surface of the flange 328 as viewed in FIG. 18. A plurality of slots 329 extend into the flange and, if desired into the extended rim 320. This embodiment is provided for surgeons who prefer to use acetabular cup members having extended rims. It should be recognized that extended rims could be used with the other embodiments of the present invention. Extended rims are well known and, in and of themselves, form no part of the present invention.

The acetabular cup member of the present invention provides a significant cost benefit in that a single acetabular cup member can be used either as a unitary acetabular cup implanted directly into the prepared cavity of an acetabulum with bone cement where the condition of the patient warrants and yet may also be used as a component with an appropriate metal shell where the condition of the patient requires the use of an acetabular cup assembly.

Many modifications of the present invention will become readily apparent to those skilled in the art. For example, among other readily apparent changes, the embodiment of FIGS. 13–17 shows the sawtooth members 250 between the flange 224 and the screw thread 256. If desired, the acetabular cup member 212 could be designed with the screw thread 256 between the flange 228 and the sawtooth members 250 provided, of course, that the metal shell 214 were designed with its screw thread 258 and sawtooth members 257 appropriately repositioned. Accordingly, the scope of the present invention should be limited only by the scope of the appended claims.

I claim:

1. An acetabular cup member suitable for use in direct implantation with bone cement and as an insert for a metal shell component of an acetabular cup assembly, said cup member having a central axis an inner face with a generally dome-shaped configuration extending from an apex lying on said axis at least a major portion of said inner face, including the portion adjacent said apex having a spherical configuration, and an outer portion opposite said inner face, said outer portion having formed therein a combination of (i) retention means engageable with engagement means on a metal shell component of a type adapted for implantation without bone cement and (ii) surface irregularities configured for retentive engagement with bone cement, said retention means comprising an outwardly extending bead and a plurality of dovetail slots in said outer portion, each of said slots having a wall parallel to said axis.

2. An acetabular cup member suitable for use in direct implantation with bone cement and as an insert for a metal shell component of an acetabular cup assembly, said cup member having a central axis, an inner face with a generally dome-shaped configuration extending from an apex lying on said axis, at least a major portion of said inner face, including the portion adjacent said apex having a spherical configuration, an outer portion opposite said inner face, an edge between said inner face and said outer portion and a flange extending outwardly from said outer portion at said edge, said outer portion having formed therein a combination of (i) retention means engageable with engagement means on a metal shell component of a type adapted for implantation without bone cement and (ii) surface irregularities configured for retentive engagement with bone cement, said retention means comprising an outwardly extending bead and a plurality of dovetail slots in said outer portion, each of said slots having a wall parallel to said axis.

3. The acetabular cup member according to claim 2, wherein said slots extend to said flange.

4. An acetabular cup member suitable for use in direct implantation with bone cement and as an insert for a metal shell component of an acetabular cup assembly, said cup member having a central axis, an inner face with a generally dome-shaped configuration extending from an apex lying on said axis, at least a major portion of said inner face, including the portion adjacent said apex having a spherical configuration, and an outer portion opposite said inner face, said outer portion having formed therein a combination of (i) retention means engageable with engagement means on a metal shell component, said retention means comprising a thread and rachet means on said outer portion and (ii) surface irregularities configured for retentive engagement with bone cement.

5. An acetabular cup member suitable for use in direct implantation with bone cement and as an insert for a metal shell component of an acetabular cup assembly, said cup member having a central axis, an inner face with a generally dome-shaped configuration extending from an apex lying on said axis, at least a major portion of said inner face, including the portion adjacent said apex having a spherical configuration, and an outer portion opposite said inner face, an edge between said inner face and said outer portion and a flange extending outwardly from said outer portion at said edge, said outer portion having formed therein a combination of (i) retention means engageable with engagement means on a metal shell component, said retention means comprising a thread and rachet means on said outer portion adjacent said flange and (ii) surface irregularities configured for retentive engagement with bone cement.

6. The acetabular cup member according to claim 5, wherein said rachet means comprises a plurality of sawtooth members having a pair of faces angling toward each other and meeting at a blunt end.

7. An acetabular cup assembly comprising (a) a cup member and (b) a metal shell, said metal shell having an internal cup-shaped surface extending from an apex to an edge, said surface sized to receive said cup member and having engagement means, said cup member having a central axis, an inner face with a generally dome-shaped configuration extending from an apex lying on said axis, at least a major portion of said inner face, including the portion adjacent said apex having a spherical configuration, and an outer portion opposite said inner face, an edge between said inner face and said outer portion and a circumferential flange extending outwardly from said outer portion at said edge and overlying said metal shell edge, said outer portion having formed therein a combination of (i) retention means engageable with said metal shell engagement means and (ii) surface irregularities, said retention means comprising an outwardly extending bead and a plurality of dovetail slots each having a rear wall parallel to said axis and a pair of sidewalls extending in convergent relationship to one another from said rear wall to said outer portion and said engagement means including a recess to receive said bead and ribs extending from said shell internal surface positioned and sized to snugly engage said dovetail slots.

8. An acetabular cup assembly comprising (a) a cup member and (b) a metal shell, said metal shell having an internal cup-shaped surface extending from an apex to an edge, said surface sized to receive said cup member and having engagement means, said cup member having a central axis, an inner face with a generally dome-shaped configuration extending from an apex lying on said axis, at least a major portion of said inner face, including the portion adjacent said apex having a spherical configuration, and an outer portion opposite said inner face, said outer portion having formed therein a combination of (i) retention means engageable with said metal shell engagement means, said retention means comprising a thread and rachet means and said engagement means comprising a thread and rachet means and (ii) surface irregularities.

9. An acetabular cup assembly comprising (a) a cup member and (b) a metal shell, said metal shell having an internal cup-shaped surface extending from an apex to an edge, said surface sized to receive said cup member and having engagement means, said cup member having a central axis, an inner face with a generally dome-shaped configuration extending from an apex lying on said axis, at least a major portion of said inner face, including the portion adjacent said apex having spherical configuration, and an outer portion opposite said inner face, an edge between said inner face and said outer portion and a circumferential flange extending outwardly from said outer portion at said edge and overlying said metal shell edge, said outer portion having formed therein a combination of (i) retention means engageable with said metal shell engagement means, said retention means comprising a plurality of sawtooth members having a pair of faces angling toward each other and meeting at a blunt end and a thread in parallel relationship with said flange and said engagement means comprises a thread and sawtooth members having a pair of faces angling toward each other and meeting at a blunt end, the sawtooth members and the threads of said cup member and said metal shell being disposed to permit said cup member to be screwed into said metal shell and preventing said cup member from being unscrewed from said metal shell and (ii) surface irregularities.

10. An acetabular cup member suitable for use in direct implantation with bone cement and as an insert for a metal shell component of an acetabular cup assembly, said cup member having a central axis, an inner face with a generally dome-shaped configuration extending from an apex lying on said axis, at least a major portion of said inner face, including the portion adjacent said apex having a spherical configuration, and an outer portion opposite said inner face, said outer portion having formed therein a combination of (i) retention means engageable with engagement means on a metal shell component of a type adapted for implantation without bone cement and (ii) surface irregularities configured for retentive engagement with bone cement, said retention means comprising at least one dovetail slot in said outer portion, said slot having a wall parallel to said axis.

11. An acetabular cup member according to claim 1, wherein each of said slots has a pair of sidewalls extending from said parallel wall to said outer portion in convergent relationship to one another.

12. An acetabular cup member according to claim 2, wherein each of said slots has a pair of sidewalls extending from said parallel wall to said outer portion in convergent relationship to one another.

13. An acetabular cup member according to claim 10, wherein each of said slots has a pair of sidewalls extending from said parallel wall to said outer portion in convergent relationship to one another.

* * * * *